US011503990B2

(12) United States Patent
Ishizeki et al.

(10) Patent No.: US 11,503,990 B2
(45) Date of Patent: Nov. 22, 2022

(54) IMAGING SYSTEM, PROCESSING DEVICE AND ILLUMINATION CONTROL METHOD TO SET EMISSION TIMING OF ILLUMINATION LIGHT IN READOUT PERIOD OF SIGNAL VALUE OF IMAGER

(71) Applicant: OLYMPUS CORPORATION, Tokyo (JP)

(72) Inventors: Manabu Ishizeki, Hino (JP); Ryohei Kagawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 205 days.

(21) Appl. No.: 16/932,891

(22) Filed: Jul. 20, 2020

(65) Prior Publication Data
US 2020/0345222 A1 Nov. 5, 2020

Related U.S. Application Data

(63) Continuation of application No. PCT/JP2019/002378, filed on Jan. 24, 2019.

(30) Foreign Application Priority Data

Feb. 9, 2018 (JP) .............................. JP2018-021867

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00006* (2013.01); *A61B 1/00009* (2013.01);
(Continued)

(58) Field of Classification Search
CPC ..... A61B 1/05; A61B 1/00096; A61B 1/0061; A61B 1/00006; A61B 1/00009;
(Continued)

(56) References Cited

U.S. PATENT DOCUMENTS

2004/0095464 A1   5/2004   Miyagi et al.
2014/0316196 A1*  10/2014  Wichern ............... A61B 1/0676
                                                              600/109
(Continued)

FOREIGN PATENT DOCUMENTS

JP   2002-172088 A   6/2002
JP   2004-166761 A   6/2004
(Continued)

OTHER PUBLICATIONS

International Search Report dated Apr. 9, 2019 issued in PCT/JP2019/002378.

*Primary Examiner* — John P Leubecker
(74) *Attorney, Agent, or Firm* — Scully, Scott, Murphy & Presser, P.C.

(57) ABSTRACT

An imaging system includes: a light source configured to emit illumination light; an imager configured to store an electric charge corresponding to an amount of received light and read out the stored electric charge as a signal value by using a rolling shutter method; a frequency detector configured to detect a vibrational frequency of a predetermined site of a subject; and an illumination controller configured to control emission of the illumination light during a readout period of the signal value. The illumination controller is configured to set a phase for an emission timing of the illumination light in an exposure period during which the imager stores the electric charge to be an identical phase at the frequency in each frame, and refer to respective phases set in exposure periods of chronologically adjacent frames to set an emission timing of the illumination light in the readout period.

17 Claims, 7 Drawing Sheets

(51) Int. Cl.
*H04N 5/225* (2006.01)
*H04N 5/235* (2006.01)

(52) U.S. Cl.
CPC ....... *A61B 1/00096* (2013.01); *H04N 5/2353* (2013.01); *H04N 2005/2255* (2013.01)

(58) Field of Classification Search
CPC .... A61B 1/045; A61B 1/2673; H04N 5/2353; H04N 2005/2255
See application file for complete search history.

(56) References Cited

U.S. PATENT DOCUMENTS

| | | | |
|---|---|---|---|
| 2016/0073865 A1* | 3/2016 | Takahashi | A61B 1/00006 600/188 |
| 2017/0064178 A1 | 3/2017 | Kagawa et al. | |
| 2019/0142264 A1* | 5/2019 | Bos | A61B 1/00006 600/188 |
| 2019/0142265 A1* | 5/2019 | Bos | A61B 7/023 600/188 |

FOREIGN PATENT DOCUMENTS

| | | |
|---|---|---|
| JP | 2016-052453 A | 4/2016 |
| JP | 2016-202380 A | 12/2016 |
| WO | 2015/194415 A1 | 12/2015 |

\* cited by examiner

IMAGING SYSTEM, PROCESSING DEVICE AND ILLUMINATION CONTROL METHOD TO SET EMISSION TIMING OF ILLUMINATION LIGHT IN READOUT PERIOD OF SIGNAL VALUE OF IMAGER

CROSS-REFERENCE TO RELATED APPLICATION

This application is a continuation of PCT International Application No. PCT/JP2019/002378 filed on Jan. 24, 2019, which designates the United States, incorporated herein by reference, and which claims the benefit of priority from Japanese Patent Application No. 2018-021867, filed on Feb. 9, 2018, incorporated herein by reference.

BACKGROUND

1. Technical Field

The present disclosure relates to an imaging system including a light source that emits illumination light and an imaging element, a processing device, and an illumination control method.

2. Related Art

In medical fields, an endoscope system is conventionally used to observe the inside of the body of a subject. In an endoscope system, generally, a flexible insertion portion having an elongated shape is inserted into the body of the subject such as a patient, illumination light is emitted from the distal end of the insertion portion, and the reflected light of the illumination light is received by an imaging unit at the distal end of the insertion portion to capture the in-vivo image. The thus captured biological image is presented on a display of the endoscope system.

When the observation target is vocal cords so as to observe the vocal-cord motion during voice production, the vocal cords are intermittently illuminated with strobe light, and the image of the vocal cords is captured (for example, see Japanese Laid-open Patent Publication No. 2002-172088). FIGS. 7 and 8 are graphs illustrating the emission timings in a conventional endoscope system. In the case of imaging with strobe light, the light is emitted at different phases (phases $P_E101$, $P_E102$, $P_E103$, . . . , $P_E108$, . . . ) shifted from the vocal-cord frequency (see FIG. 7). Here, the vocal cords are illuminated multiple number of times at different phases in a time period (e.g., frame periods F101 and F102) corresponding to one frame. In Japanese Laid-open Patent Publication No. 2002-172088, in order to suppress the blurring of an image due to multiple light emissions in one frame, the emission timings in the identical frame are set to be emitted at identical phases (phases $P_E111$, $P_E112$, $P_E113$, . . . ) (see FIG. 8).

SUMMARY

In some embodiments, an imaging system includes: a light source configured to emit illumination light; an imager configured to store an electric charge corresponding to an amount of received light and read out the stored electric charge as a signal value by using a rolling shutter method; a frequency detector configured to detect a vibrational frequency of a predetermined site of a subject; and an illumination controller configured to control emission of the illumination light during a readout period of the signal value. The illumination controller is configured to set a phase for an emission timing of the illumination light in an exposure period during which the imager stores the electric charge to be an identical phase at the frequency in each frame, and refer to respective phases set in exposure periods of chronologically adjacent frames to set an emission timing of the illumination light in the readout period.

In some embodiments, provided is a processing device configured to be connected to an endoscope including an imager configured to read out an electric charge stored in a pixel by using a rolling shutter method. The processing device includes: a frequency detector configured to detect a frequency of a predetermined site of a subject; and an illumination controller configured to control emission of the illumination light during a readout period of the signal value. The illumination controller is configured to set a phase for an emission timing of the illumination light in an exposure period during which the imager stores the electric charge to be an identical phase at the frequency in each exposure period, and refer to respective phases set in exposure periods of chronologically adjacent frames to set an emission timing of the illumination light in the readout period.

In some embodiments, provided is an illumination control method implemented by an imaging system including: a light source configured to emit illumination light; and an imager configured to store an electric charge corresponding to an amount of received light and read out the stored electric charge as a signal value by using a rolling shutter method. The illumination control method includes: detecting a vibrational frequency of a predetermined site of a subject; setting a phase for an emission timing of the illumination light in an exposure period during which the imager stores the electric charge to be an identical phase at the frequency in each frame; and referring to respective phases set in exposure periods of chronologically adjacent frames to set an emission timing of the illumination light in a readout period of the signal value.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
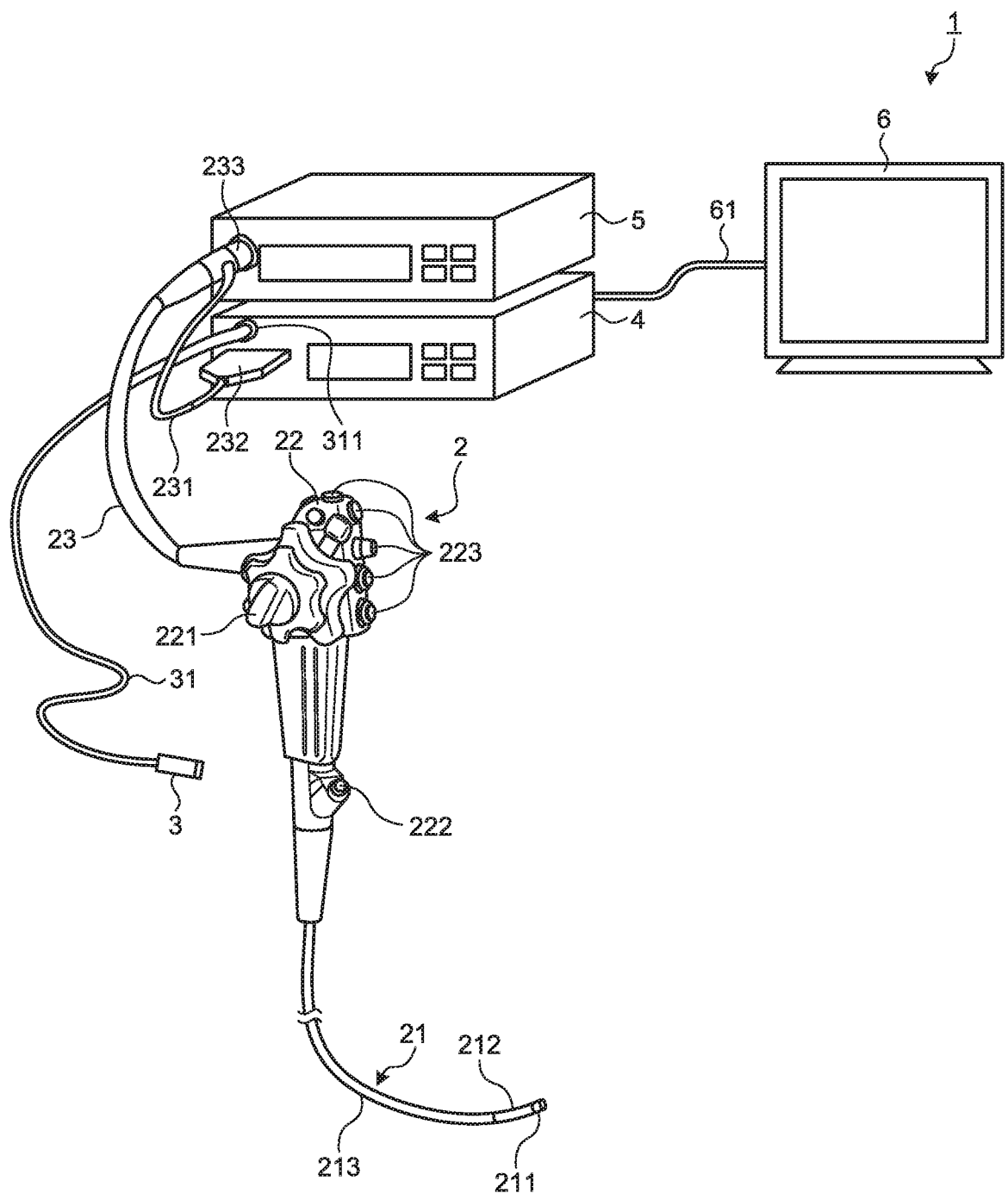
FIG. 1 is a diagram illustrating a schematic configuration of an endoscope system according to a first embodiment of the disclosure.

Modes (hereinafter referred to as "embodiments") for carrying out the disclosure are described below. In the embodiments, a medical endoscope system that captures and displays an image inside the body cavity of a subject, such as a patient, is described as an example of an imaging system according to the disclosure. The disclosure is not limited to the embodiments. In the description of the drawings, the same components are denoted by the same reference numeral.

First Embodiment

FIG. 1 is a schematic view illustrating a schematic configuration of an endoscope system according to a first embodiment of the disclosure. As illustrated in FIG. 1, an endoscope system 1 according to the first embodiment includes: an endoscope 2 (scope) that is introduced into the body of the subject to capture the image inside the body of the subject and generate the image signal of the inside of the subject's body; a voice input device 3 that receives a voice; a processing device 4 that performs predetermined image processing on the imaging signal captured by the endoscope 2 and controls each unit of the endoscope system 1; a light source device 5 (light source unit) that generates pulsed light as illumination light (observation light) of the endoscope 2; and a display device 6 that displays the image corresponding to the image signal generated by the processing device 4 after image processing.

The endoscope 2 includes: an insertion portion 21 that is inserted into the subject; an operating unit 22 that is provided on the proximal end side of the insertion portion 21 so as to be grasped by the operator; and a flexible universal cord 23 that extends from the operating unit 22.

The insertion portion 21 is implemented by using an illumination fiber (light guide cable), an electric cable, etc. The insertion portion 21 includes: a distal end portion 211 including an imaging unit having a built-in imaging element that captures the inside of the subject; a bendable curved portion 212 including a plurality of bendable pieces; and a flexible tube portion 213 having flexibility and provided on the proximal end side of the curved portion 212. The distal end portion 211 includes an illumination unit that illuminates the inside of the subject via an illumination lens; an observation unit that captures the inside of the subject; an opening that communicates with a treatment tool channel; and an air/water supply nozzle (not illustrated).

The operating unit 22 includes: a curving knob 221 that curves the curved portion 212 in a vertical direction and a horizontal direction; a treatment tool insertion portion 222 through which a treatment tool, such as biopsy forceps or a laser scalpel, is inserted into the body cavity of the subject; and a plurality of switch portions 223 that operate peripheral devices such as the processing device 4, the light source device 5, an air supply device, a water supply device, or a gas supply device. A treatment tool inserted through the treatment tool insertion portion 222 is exposed from an opening at the distal end of the insertion portion 21 via the treatment tool channel provided inside.

The universal cord 23 is configured by using an illumination fiber, an electric cable, etc. The universal cord 23 branches at the proximal end thereof so that the end of a branch cord 231, which is one of the branches, is a connector 232 and the proximal end of the other one is a connector 233. The connector 232 is attachable to and detachable from the processing device 4, and the connector 233 is attachable to and detachable from the light source device 5. The universal cord 23 propagates the illumination light emitted from the light source device 5 to the distal end portion 211 via the connector 232, the operating unit 22, and the flexible tube portion 213. The universal cord 23 transmits the imaging signal captured by the imaging unit provided in the distal end portion 211 to the processing device 4.

An illumination fiber 214 (see FIG. 2) that guides illumination light from the light source device 5 is disposed in the insertion portion 21 and the universal cord 23. One end of the illumination fiber 214 is located at the distal end surface of the insertion portion 21, and the other end thereof is located at the connection surface between the universal cord 23 and the light source device 5.

The voice input device 3 receives the input of a voice generated by vocal cords when the object of capturing is the vocal cords. The distal end of a cord 31 is coupled to the voice input device 3, and a connector 311 at the proximal end is attachable to and detachable from the processing device 4. The voice input device 3 outputs the input voice to the processing device 4 via the cord 31 and the connector 311. The voice input device 3 corresponds to a vocal-cord vibration input unit.

The processing device 4 performs predetermined image processing on the imaging signal on the inside of the subject's body captured by the imaging unit in the distal end portion 211 of the endoscope 2 and input via the universal cord 23. The processing device 4 controls each unit of the endoscope system 1 based on various instruction signals transmitted from the switch portion 223 in the operating unit 22 of the endoscope 2 via the universal cord 23.

The light source device 5 is configured by using a light source that emits pulsed white light as illumination light (hereinafter referred to as pulsed light), a condenser lens, etc. The light source device 5 receives a light control signal from the processing device 4 and performs PWM (Pulse Width Modulation) control on the driving timing (light emission period) for driving the light source based on the light control signal. Accordingly, the light source device 5 emits pulsed light by pulse driving under the control of an illumination controller 408. The light source device 5 feeds the pulsed light from the light source to the endoscope 2 coupled thereto via the connector 232 and the universal cord 23 (the illumination fiber) as illumination light for illuminating (intermittently illuminating) the inside of the subject's body that is the object of capturing.

The display device 6 is configured by using a display, or the like, using a liquid crystal or an organic EL (Electro Luminescence). The display device 6 presents various types of information including the image corresponding to the display image signal generated by the processing device 4 via a video cable 61. This allows the operator to observe the desired position inside the subject and determine the properties while viewing the image (in-vivo image) presented by the display device 6 and operating the endoscope 2.

Figure 2:
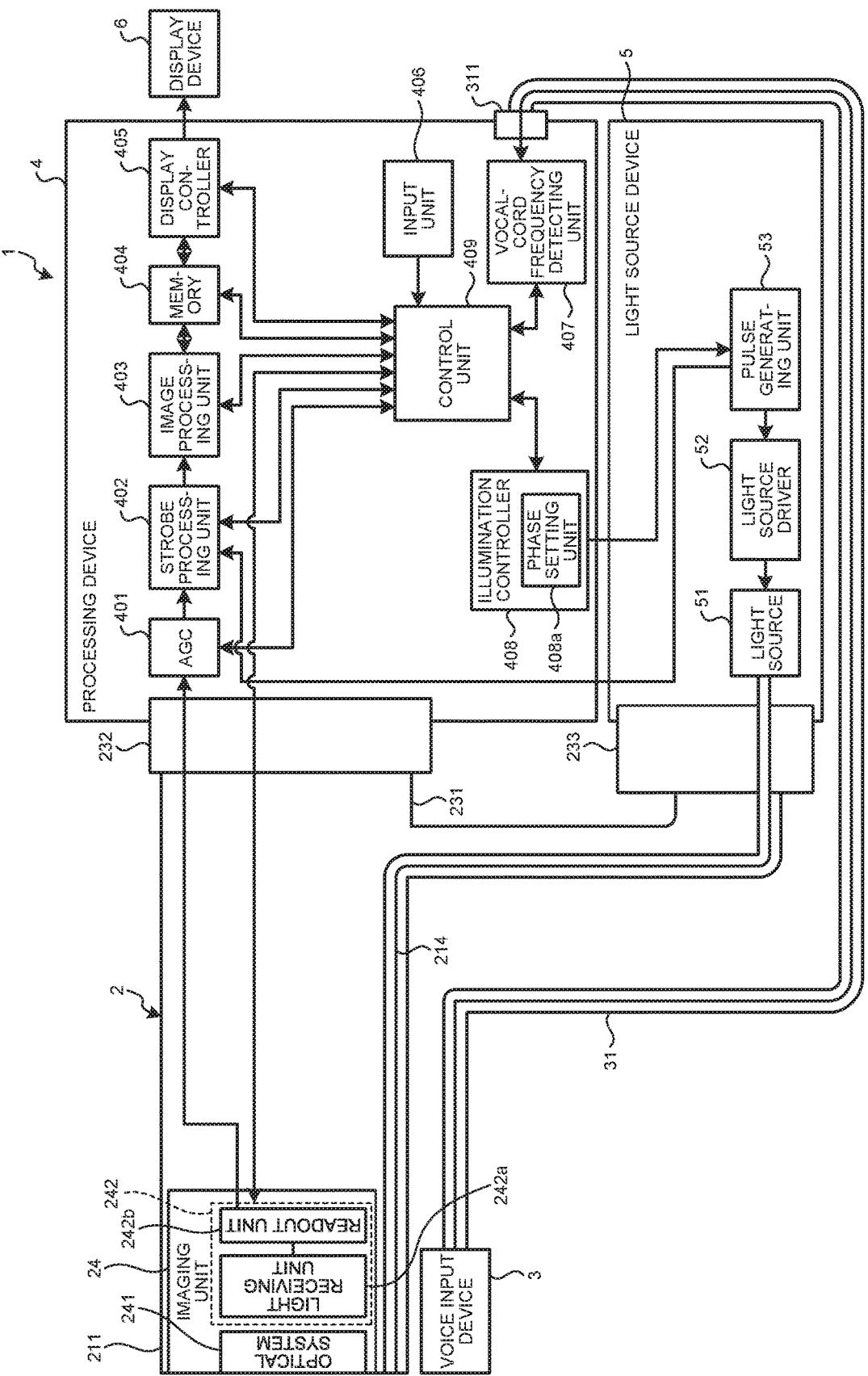
FIG. 2 is a block diagram illustrating a schematic configuration of the endoscope system according to the first embodiment of the disclosure.

Next, configurations of the endoscope 2, the voice input device 3, the processing device 4, and the light source device 5 illustrated in FIG. 1 are described. FIG. 2 is a block diagram schematically illustrating a configuration of the endoscope system 1.

The endoscope 2 includes an imaging unit 24 at the distal end portion 211. The imaging unit 24 includes: an optical system 241 such as an objective lens disposed on the light receiving surface side of a light receiving unit 242a which is described later; and an imaging element 242 that is provided at the imaging position of the optical system 241 to receive the light condensed by the optical system 241 and execute photoelectric conversion to obtain an electric signal.

The imaging element 242 is implemented by using a CMOS (Complementary Metal Oxide Semiconductor) image sensor. The imaging element 242 includes the light receiving unit 242a and a readout unit 242b.

The light receiving unit 242a receives, with the light receiving surface, the light from the object illuminated with the pulsed light from the light source device 5 and executes the photoelectric conversion on the received light to generate an electric signal. Specifically, the light receiving unit 242a includes a plurality of pixels arranged in a matrix and each having, for example, a photodiode that stores the electric charge corresponding to the amount of light and a capacitor that converts the electric charge transferred from the photodiode into a voltage level (signal value), and each of the pixels executes the photoelectric conversion on the light from the optical system 241 to generate an electric signal. In the light receiving unit 242a, two or more pixels are arranged in a pixel row (horizontal line) in a horizontal direction, and the pixel rows are arranged in a vertical direction.

The readout unit 242b sequentially reads the electric signal (signal value) generated by any pixel that is set as the readout target among the pixels of the light receiving unit 242a and outputs the electric signal as an imaging signal. The readout unit 242b executes the exposure on the pixels in the light receiving unit 242a and the readout of electric signals from the pixels. The readout unit 242b sequentially reads the electric signal generated by each of the pixels arranged in a matrix in each horizontal line (pixel row). The readout unit 242b generates an imaging signal by using a rolling shutter method, that is, performs the imaging operation including the exposure and the readout, starting from the horizontal line at the beginning, shifts the timing in each horizontal line, and executes the electric charge reset (the reset of the capacitor), the exposure, and the readout.

Thus, in the imaging unit 24, the exposure timing and the readout timing are different in each horizontal line even during one imaging period (frame). The readout unit 242b outputs the electric signal (imaging signal) read from the pixels of the light receiving unit 242a to the processing device 4 via a cable (not illustrated) and the connector 232.

Next, the processing device 4 is described. The processing device 4 includes an AGC (Auto Gain Control) 401, a strobe processing unit 402, an image processing unit 403, a memory 404, a display controller 405, an input unit 406, a vocal-cord frequency detecting unit 407, the illumination controller 408, and a control unit 409. According to the present embodiment, the processing device 4, the endoscope 2, and the light source device 5 operate in accordance with a clock signal generated by a clock generator (not illustrated) provided in the processing device 4.

The AGC 401 adjusts the amplification factor (gain) of an electric signal to maintain a constant output level. The AGC 401 is configured by using a general-purpose processor such as a CPU (Central Processing Unit) or a dedicated processor such as various arithmetic circuitries that execute a specific function, e.g., an ASIC (Application Specific Integrated Circuit) or an FPGA (Field Programmable Gate Array) that is a programmable logic device capable of rewriting the processing contents.

The strobe processing unit 402 acquires a PWM signal for controlling the intermittent illumination with pulsed light from the light source device 5 and outputs an imaging signal input from the AGC 401 in association with the PWM signal to the image processing unit 403. The strobe processing unit 402 is configured by using a general-purpose processor such as a CPU or a dedicated processor such as various arithmetic circuitries that execute a specific function, e.g., an ASIC or an FPGA.

The image processing unit 403 executes predetermined signal processing on the electric signals (imaging signals) of the pixels read by the readout unit 242b of the imaging unit 24 to generate image signals. For example, the image processing unit 403 performs, on an imaging signal, image processing including at least an optical black subtraction process, a white balance (WB) adjustment process, a synchronization process in the case of an imaging element having the Bayer arrangement, a color matrix calculation process, a gamma correction process, a color reproduction process, an edge enhancement process, and the like. The image processing unit 403 is configured by using a general-purpose processor such as a CPU or a dedicated processor such as various arithmetic circuitries that execute a specific function, e.g., an ASIC or an FPGA.

The memory 404 stores various programs for operating the processing device 4 and the light source device 5. The memory 404 temporarily stores the information that is being processed by the processing device 4. The memory 404 stores the imaging signals, read by the readout unit 242b, corresponding to the matrix arrangement of the pixels in the light receiving unit 242a in units of frame. The memory 404 stores the image signals generated by the image processing unit 403 in units of frame. The memory 404 is configured by using a RAM (Random Access Memory), a ROM (Read Only Memory), and the like. The memory 404 may be configured by using a memory card, or the like, attached at the outside of the processing device 4.

The display controller 405 selects a display image signal from the image signals of frames generated by the image processing unit 403 in accordance with the display cycle of the display device 6 and outputs the selected image signal as the image signal to be displayed on the display device 6. Alternatively, the display controller 405 combines the image signals of frames generated by the image processing unit 403 for each display period of the display device 6 to generate a display image signal and outputs it to the display device 6. The display controller 405 converts the display image signal from a digital signal into an analog signal, changes the format of the analog image signal after the conversion into a format such as a high-definition format, and outputs it to the display device 6. The display controller 405 is configured by using a general-purpose processor such as a CPU or a dedicated processor such as various arithmetic circuitries that execute a specific function, e.g., an ASIC or an FPGA.

The input unit 406 is implemented by using an operating device such as a mouse, a keyboard, or a touch panel to receive the input of various types of instruction information (instruction signals) of the endoscope system 1. Specifically, the input unit 406 receives the input of various types of instruction information such as subject information (e.g., the ID, the date of birth, or the name), the identification information (e.g., the ID or examination corresponding item) on the endoscope 2, or examination content.

The vocal-cord frequency detecting unit 407 detects the frequency (vocal-cord frequency) of the voice (the vibration of vocal cords) input to the voice input device 3 and input to the processing device 4 via the cord 31 and the connector 311. According to the first embodiment, the voice is generated from the vocal cords of the subject. The vocal-cord frequency detecting unit 407 outputs the detected frequency of the voice to the control unit 409. The vocal-cord frequency detecting unit 407 is configured by using a general-purpose processor such as a CPU or a dedicated processor such as various arithmetic circuitries that execute a specific function, e.g., an ASIC or an FPGA.

The illumination controller 408 controls the operation of the light source device 5. Specifically, the illumination controller 408 controls the emission timing and the illumination period of pulsed light from a light source 51 in synchronization with the frequency of the voice detected by the vocal-cord frequency detecting unit 407. The illumination controller 408 generates the pulse for driving the light source 51 based on the vocal-cord frequency detected by the vocal-cord frequency detecting unit 407 and the preset light emission period (the pulse width or the duty ratio), generates the light-source control PWM signal including the pulse, and outputs it to a pulse generating unit 53. The illumination controller 408 outputs the generated PWM signal to the control unit 409. The illumination controller 408 is configured by using a general-purpose processor such as a CPU or a dedicated processor such as various arithmetic circuitries that execute a specific function, e.g., as an ASIC or an FPGA.

The illumination controller 408 includes a phase setting unit 408a. The phase setting unit 408a sets the phase for emitting the strobe light with regard to the vocal-cord vibration (vocal-cord frequency). The phase setting of the strobe emission by the phase setting unit 408a is described later.

The control unit 409 controls the processing operation of each unit of the processing device 4. The control unit 409 executes, for example, the transfer of instruction information and data to each component of the processing device 4 so as to control the operation of the processing device 4. The control unit 409 is coupled to the imaging unit 24 and the light source device 5 via each cable. The control unit 409 also controls the operation of the imaging unit 24. In the description according to the present embodiment, the imaging element 242 and the light source 51 are driven at the synchronized imaging timing and illumination timing under the control of the control unit 409. The control unit 409 is configured by using a general-purpose processor such as a CPU or a dedicated processor such as various arithmetic circuitries that execute a specific function, e.g., an ASIC or an FPGA.

Next, the light source device 5 is described. The light source device 5 includes the light source 51, a light source driver 52, and a pulse generating unit 53.

The light source 51 is configured by using a light source such as a white LED that emits pulsed white light (pulsed light) and an optical system such as a condenser lens. The light source 51 generates the illumination light to be supplied to the endoscope 2 and guides the illumination light to the endoscope 2 via an illumination fiber, etc.

The light source driver 52 supplies a predetermined electric power to the light source 51 based on the PWM signal generated by the pulse generating unit 53. Accordingly, the subject is illuminated with the light (pulsed light) that is emitted from the light source 51 through the distal end portion 211 of the insertion portion 21 via the connector 233 and the universal cord 23.

The pulse generating unit 53 generates the pulse for driving the light source 51 based on the PWM signal acquired from the illumination controller 408, generates the light source control signal including the pulse, and outputs it to the light source driver 52.

Figure 3:
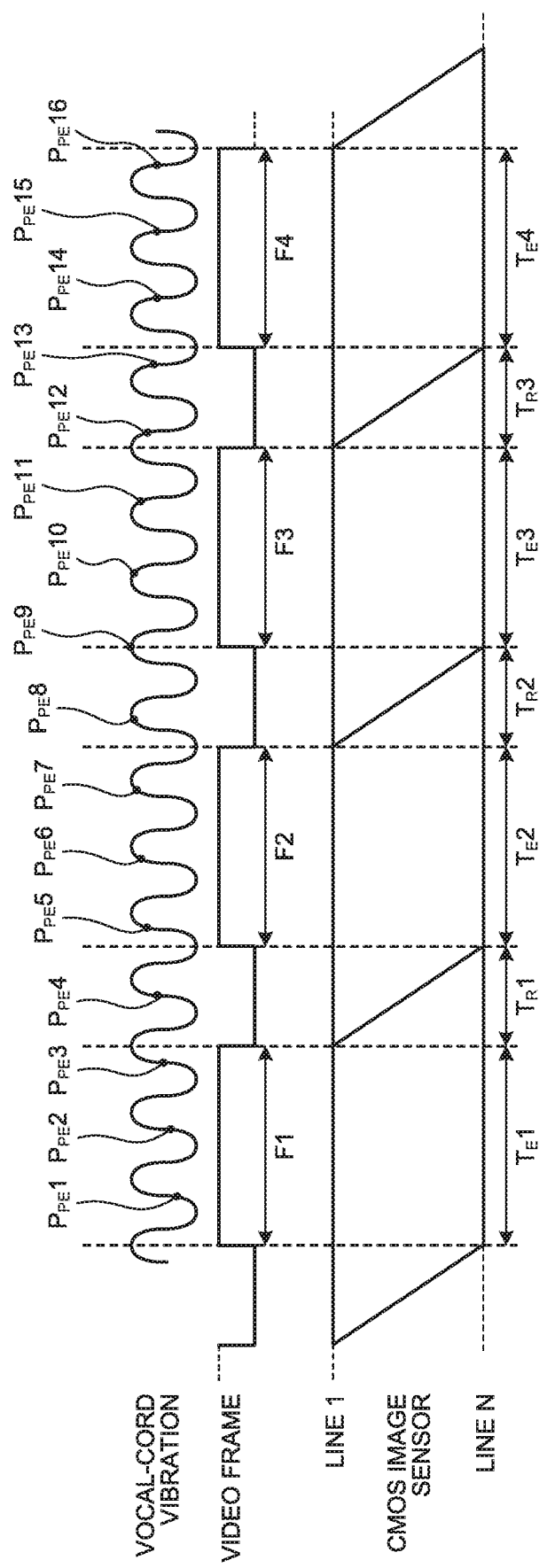
FIG. 3 is a graph illustrating a strobe emission process performed by an illumination controller of the endoscope system according to the first embodiment of the disclosure.
Figure 4:
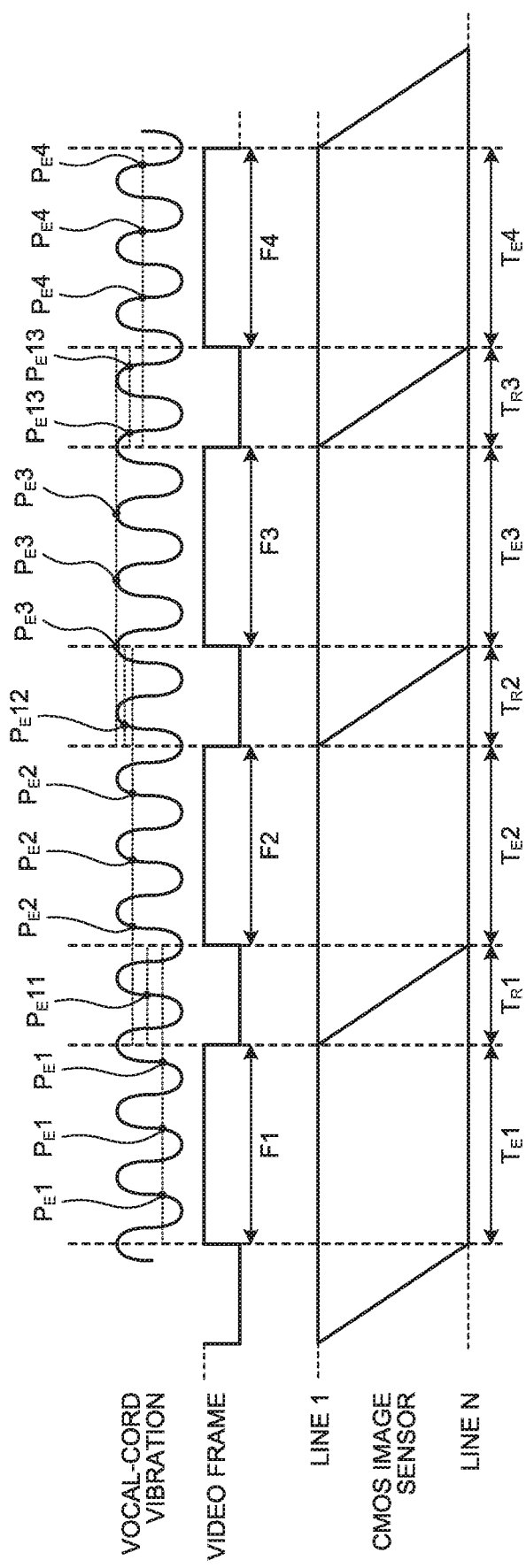
FIG. 4 is a graph illustrating a strobe emission process performed by an illumination controller of the endoscope system according to the first embodiment of the disclosure.

Next, the phase setting of the strobe emission by the phase setting unit 408a is described with reference to FIGS. 3 and 4. FIGS. 3 and 4 are graphs illustrating the strobe emission process performed by the illumination controller of the endoscope system according to the first embodiment of the disclosure. In the case of the imaging with the strobe emission, the emission is executed while the phase is shifted in the vocal-cord frequency. The phase setting unit 408a sets the phases (phases $P_{PE}1$, $P_{PE}2$, $P_{PE}3$, ..., $P_{PE}16$, ...) of temporary emission timings with regard to the vocal-cord vibration (vocal-cord frequency) illustrated in FIG. 3. During the strobe emission executed at the temporary emission timings, the illumination light is intermittently emitted while the phase is slightly shifted in one cycle as described above. For this reason, in each frame (frames F1, F2, F3, F4, ...), the illumination light is emitted multiple number of times to the vocal cord in different phases, that is, in different open states. The term "frame" here corresponds to a time period during which all the pixels are exposed and the time period during which one image is displayed on the display device 6.

The phase setting unit 408a refers to the readout timing of the readout unit 242b to set the readout period and the full exposure period of the imaging operation performed by the imaging unit 24. For example, as illustrated in FIG. 3, the phase setting unit 408a sets total readout periods $T_R1$, $T_R2$, $T_R3$, ..., from the line (a line 1) for starting the readout to the last line (a line N: N is a natural number equal to or more than two). Then, the phase setting unit 408a sets full exposure periods $T_E1$, $T_E2$, $T_E3$, $T_E4$, ..., which are provided between the chronologically adjacent total readout periods and during which all the pixels store the electric charge. The full exposure periods $T_E1$, $T_E2$, $T_E3$, $T_E4$, ..., are synchronized with the frames (video frames) F1, F2, F3, F4, ..., respectively, each frame being for displaying one image.

Then, with regard to the full exposure periods $T_E1$, $T_E2$, $T_E3$, $T_E4$, ..., the phase setting unit 408a sets a phase for the strobe emission in each full exposure period. According to the first embodiment, the phase setting unit 408a sets a first phase in each full exposure period as each of emission phases (phases for the strobe emission) in the full exposure period. As illustrated in for example FIG. 4, the phase setting unit 408a sets the emission timings in the full exposure period $T_E1$ to be emitted at the identical phases. During the full exposure period $T_E1$, each of the phases at the temporary emission timings is set to be a phase $P_E1$ that is identical to the phase $P_{PE}1$ at the first emission timing. Specifically, during the full exposure period $T_E1$, each of the phases $P_{PE}2$ and $P_{PE}3$ illustrated in FIG. 3 is changed to the phase $P_E1$ that is identical to the phase $P_{PE}1$. Similarly, the phase setting unit 408a sets the phases $P_E2$, $P_E3$, $P_E4$, ..., which are identical to the phases $P_{PE}5$, $P_{PE}9$, and $P_{PE}14$, ..., respectively, as each of phases for the strobe emission in each of the full exposure periods $T_E2$, $T_E3$, $T_E4$, .... Due to the phase setting described above, the subject's vocal cords having the identical open state are illuminated in each frame. Thus, the image acquired during the full exposure period is the vocal-cord image having less blurring or unevenness in brightness. In the example described according to the first embodiment, the phase at the first emission timing in each of the full exposure periods is set as each of the phases for the strobe emission in the full exposure period; however, the average value of phases at the emission timings included in the full exposure period may be set as each of the phases for the strobe emission in the full exposure period.

After setting the phases of the full exposure periods $T_E1$, $T_E2$, $T_E3$, $T_E4$, ..., the phase setting unit 408a sets the phase for the emission in each of the total readout periods $T_R1$, $T_R2$, $T_R3$, .... The phase setting unit 408a calculates the average of the phases set in the frames previous to and subsequent to the readout period and sets the averaged phase as the emission phase in the total readout period.

As illustrated in for example FIG. 4, with regard to the total readout period $T_R1$, the phase setting unit 408a calculates the average value of the phase $P_{E1}$ set in the frame F1 and the phase $P_E2$ set in the frame F2 and sets the averaged phase (a phase $P_E11$) as the phase for the strobe emission. Similarly, with regard to the total readout periods $T_R2$, $T_R3$, ..., the phase setting unit 408a sets the phases (phases $P_E12$, $P_E13$, ...), which are the average of the phases in the adjacent frames, as the phase for the strobe emission. As the exposure processes for two frames are mixed during the readout period, the emission at the intermediate phase between the phases in the two frames enables the averaging of blurring that occurs in the frames.

The illumination controller 408 generates a PWM signal based on the phase set by the phase setting unit 408a. The pulse generating unit 53 generates a pulse based on the acquired PWM signal so as to drive the light source driver 52 and cause the light source 51 to emit the strobe. All of the strobe emissions have the same emission intensity. The emission intensities in the full exposure period and the total readout period may be set to be different from each other.

According to the first embodiment described above, with regard to the full exposure periods $T_E1$, $T_E2$, $T_E3$, $T_E4$, ..., each of the phases for the strobe emission in the frame is set to be the identical phase and, with regard to the total readout periods $T_F1$, $T_R2$, $T_R3$, ..., the average of the phases set in the adjacent frames is calculated and the averaged phase is set as the emission phase in the total readout period. According to the first embodiment, even in the case of sequential imaging using the rolling shutter method, it is possible to suppress blurring of a vocal-cord image.

Second Embodiment

Figure 5:
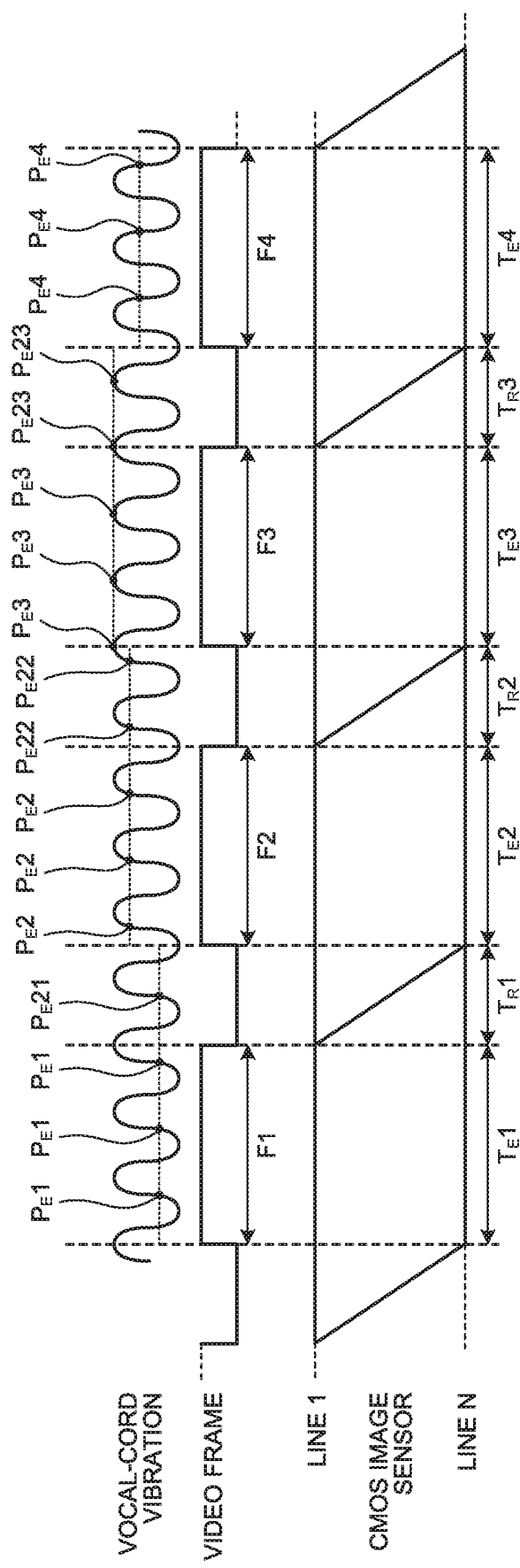
FIG. 5 is a graph illustrating a strobe emission process performed by the illumination controller of the endoscope system according to a second embodiment of the disclosure.

Next, a second embodiment of the disclosure is described. An endoscope system according to the second embodiment has the same configuration as that of the above-described endoscope system 1. The second embodiment is different from the first embodiment described above in the phase setting during the readout period. A setting process, which is different from that in the first embodiment described above, is described with reference to FIG. 5. FIG. 5 is a graph illustrating a strobe emission process performed by the illumination controller of the endoscope system according to the second embodiment of the disclosure.

The phase setting unit 408a sets a phase for the strobe emission in each of the full exposure periods $T_E1$, $T_E2$, $T_E3$, $T_E4$, ..., in the same manner as in the first embodiment. Specifically, the phase setting unit 408a sets a first phase in each full exposure period as each of emission phases in the full exposure period. As illustrated in for example FIG. 5, the phase setting unit 408a sets phases for the strobe emission in the full exposure periods $T_E1$, $T_E2$, $T_E3$, $T_E4$, ... to be the phases $P_E1$, $P_E2$, $P_E3$, $P_E4$, ..., respectively.

After setting the phases in the full exposure periods $T_E1$, $T_E2$, $T_E3$, $T_E4$, ..., the phase setting unit 408a sets the respective phases for the emission in the total readout periods $T_R1$, $T_R2$, $T_R3$, .... According to the second embodiment, the phase setting unit 408a sets the phase in the chronologically previous frame out of the phases set in the frames previous to and subsequent to the readout period as the emission phase in the total readout period. As illustrated in for example FIG. 5, with regard to the total readout period $T_R1$, the phase setting unit 408a sets the phase (a phase $P_E21$) identical to the phase $P_E1$ set in the frame F1 as the phase for the strobe emission. Similarly, with regard to the total readout periods $T_R2$, $T_R3$, ..., the phase setting unit 408a sets the phases (phases $P_E22$, $P_E23$, ...) identical to the phases $P_E2$, $P_E3$, ... in the frame before the readout period as the phase for the strobe emission, respectively.

The illumination controller 408 generates a PWM signal based on the phase set by the phase setting unit 408a. The pulse generating unit 53 generates a pulse based on the acquired PWM signal so as to drive the light source driver 52 and cause the light source 51 to emit the strobe. According to the second embodiment, the emission intensity in the total readout period is set to be lower than the emission intensity in the full exposure period.

According to the second embodiment described above, with regard to the full exposure period, each of the phases for the strobe emission in the frame is set to be the identical phase, with regard to the total readout period, the phase set in the frame before the total readout period is set as the emission phase in the total readout period, and the emission intensity in the total readout period is set to be lower than the emission intensity in the full exposure period. Thus, even though the phase in the frame after the readout period is different from the phase in the full exposure period, the effect of blurring of a vocal-cord image due to the exposure in the total readout period may be reduced. According to the second embodiment, even in the case of sequential imaging using the rolling shutter method, it is possible to suppress the blurring of a vocal-cord image.

Modification of the Second Embodiment

Figure 6:
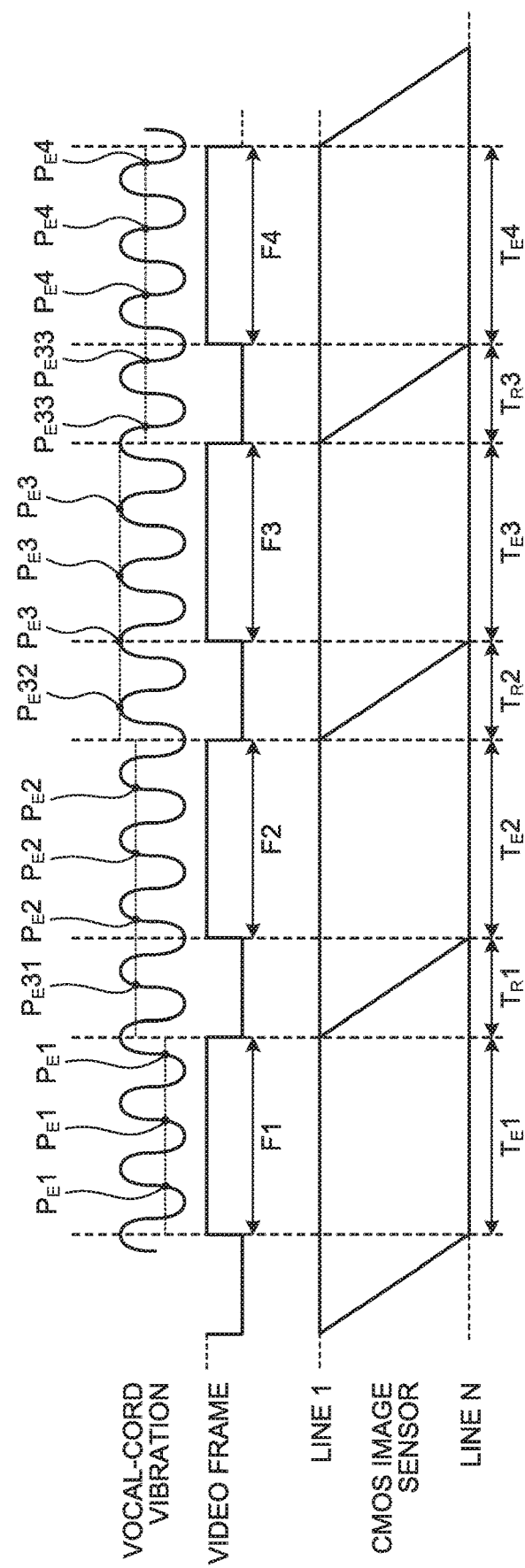
FIG. 6 is a graph illustrating a strobe emission process performed by the illumination controller of the endoscope system according to a modification of the second embodiment of the disclosure.
Figure 7:
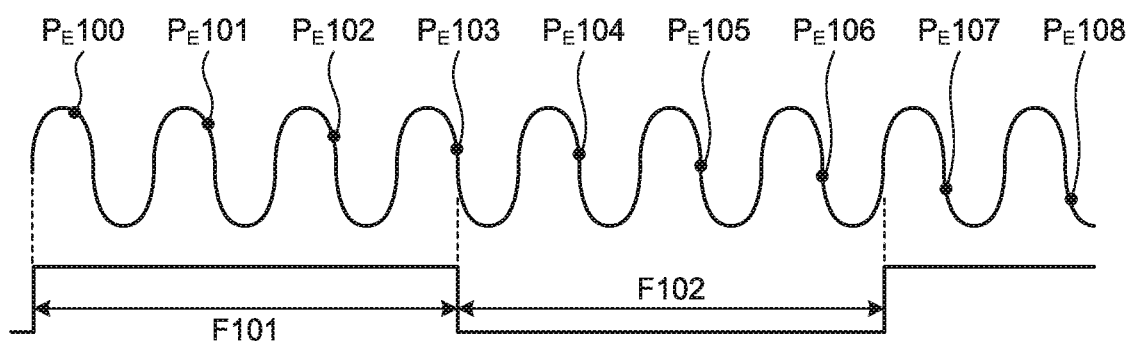
FIG. 7 is a graph illustrating emission timings in a conventional endoscope system.
Figure 8:
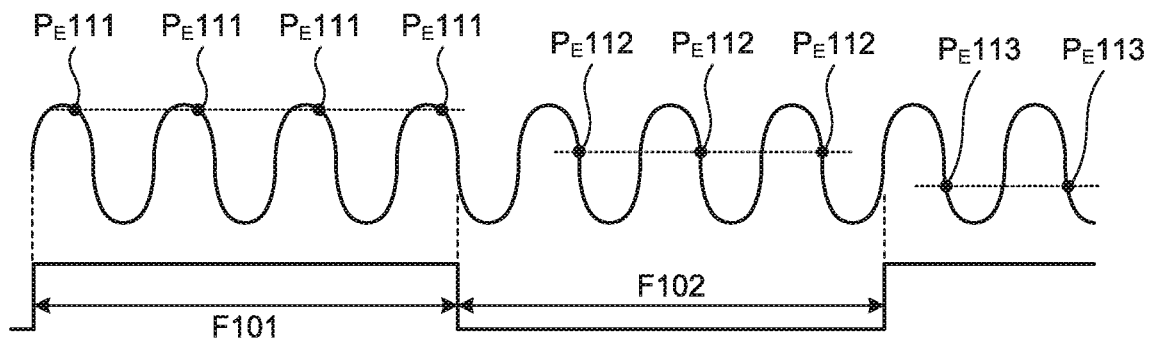
FIG. 8 is a graph illustrating emission timings in a conventional endoscope system.

Next, a modification of the second embodiment of the disclosure is described. An endoscope system according to the present modification has the configuration similar to that of the above-described endoscope system 1. The present modification is different from the above-described second embodiment in the phase setting during the readout period. A setting process different from that in the above-described second embodiment is described below with reference to FIG. 6. FIG. 6 is a graph illustrating a strobe emission process performed by the illumination controller of the endoscope system according to the modification of the second embodiment of the disclosure.

The phase setting unit 408a sets a phase for the strobe emission in each of the full exposure periods $T_E1$, $T_E2$, $T_E3$, $T_E4$, ..., in the same manner as in the first embodiment and the second embodiment. Specifically, the phase setting unit 408a sets a first phase in each full exposure period as each of emission phases in the full exposure period.

After setting the phases in the full exposure periods $T_E1$, $T_E2$, $T_E3$, $T_E4$, ..., the phase setting unit 408a sets the phase for the emission in each of the total readout periods $T_R1$, $T_R2$, $T_R3$, .... According to the present modification, the phase setting unit 408a sets the phase in the chronologically subsequent frame out of the phases set in the frames previous to and subsequent to the readout period as the emission phase in the total readout period. As illustrated in for example FIG. 6, with regard to the total readout period $T_R1$, the phase setting unit 408a sets the phase (a phase $P_E31$) identical to the phase $P_E2$ set in the frame F2 as the phase for the strobe emission. Similarly, with regard to the total readout periods $T_R2, T_R3, \ldots$, the phase setting unit 408a sets the phases (phases $P_E32, P_E33, \ldots$) identical to the phases $P_E3, P_E4, \ldots$ in the frame after the readout period as the phase for the strobe emission, respectively.

The illumination controller 408 generates a PWM signal based on the phase set by the phase setting unit 408a. The pulse generating unit 53 generates a pulse based on the acquired PWM signal so as to drive the light source driver 52 and cause the light source 51 to emit the strobe. According to the present modification, the emission intensity in the total readout period is set to a value lower than the emission intensity in the full exposure period.

According to the modification described above, with regard to the full exposure period, each of the phases for the strobe emission in the frame is set to be the identical phase, with regard to the total readout period, the phase set in the frame after the total readout period is set as the emission phase in the total readout period, and the emission intensity in the total readout period is set to be a value lower than the emission intensity in the full exposure period. Thus, even though the phase in the frame before the readout period is different from the phase in the full exposure period, the effect of blurring of a vocal-cord image due to the exposure in the total readout period may be reduced. According to the present modification, even in the case of sequential imaging using the rolling shutter method, it is possible to suppress the blurring of a vocal-cord image.

In addition to the phase setting example according to the above-described modification, the average of the phases in the adjacent frames as described above in the first embodiment may be set as the phase in the total readout period, or the conventionally set phase illustrated in FIG. 3, e.g., the intermediate phase between the phases set in the full exposure periods of the adjacent frames may be set as the phase in the total readout period.

In the first embodiment and the second embodiment described above, it is possible to provide a rotary filter including a plurality of filters that is arranged on the optical path of white light (illumination light) emitted from the light source 51 to rotate so as to exclusively allow the passage of light having a predetermined wavelength band included in the white light. The provided rotary filter allows the light having an individual wavelength band, such as red light (R), green light (G), and blue light (B), to be sequentially transmitted and emitted. By controlling the rotation of the rotary filter in accordance with the emission timing of pulsed light, any of red light (R illumination), green light (G illumination), and blue light (B illumination) having a narrow band, included in the white light emitted from the light source 51, may be sequentially emitted to the endoscope 2 (sequential lighting). Instead of the rotary filter, it is possible to use a light source (e.g., an LED light source) that emits the light having a wavelength band for each color.

In the description according to the first embodiment and the second embodiment described above, the imaging element 242 operates under the control of the control unit 409; however, the illumination controller 408 (the phase setting unit 408a) may be provided at the side of the endoscope 2 so that the strobe emission is controlled at the side of the endoscope 2. In the description, the imaging element 242 operates based on the clock signal generated by the processing device 4; however, a clock generator may be provided in the endoscope 2 so that the imaging element 242 operates based on the clock signal generated by the clock generator (the clock signal generated by the endoscope 2), or the imaging element 242 may operate based on a clock signal generated by an external clock generator.

In the description according to the first embodiment and the second embodiment described above, the AGC 401 is provided in the processing device 4; however, the AGC 401 may be provided in the endoscope 2 (e.g., the imaging unit 24).

In the description according to the first embodiment and the second embodiment described above, the object is a vocal cord; however, any object other than a vocal cord is applicable as long as the object vibrates at a high speed and the frequency thereof is detectable by the vocal-cord frequency detecting unit 407.

As described above, the imaging system according to the disclosure is useful in suppressing the blurring of an image even in the case of application of a rolling shutter method.

According to the disclosure, it is possible to produce an advantage such that the blurring of an image may be suppressed even in the case of application of a rolling shutter method.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
    a light source configured to emit illumination light;
    an imager configured to store an electric charge corresponding to an amount of received light and read out the stored electric charge as a signal value by using a rolling shutter method;
    a frequency detector configured to detect a vibrational frequency of a predetermined site of a subject; and
    an illumination controller configured to control emission of the illumination light during a readout period of the signal value, wherein the illumination controller is configured to:
        set a phase for an emission timing of the illumination light in an exposure period during which the imager stores the electric charge to be an identical phase at the frequency in each frame; and
        refer to respective phases set in exposure periods of chronologically adjacent frames to set an emission timing of the illumination light in the readout period.

2. The imaging system according to claim 1, wherein the illumination controller is configured to:
    set a phase for the emission timing of the illumination light in the readout period to be an average of respective phases set in the exposure periods of chronologically adjacent frames; and
    match an emission intensity of the illumination light in the readout period with an emission intensity of the illumination light in the exposure period during which the imager stores the electric charge.

3. The imaging system according to claim 1, wherein the illumination controller is configured to set an emission intensity of the illumination light in the readout period to be lower than an emission intensity of the illumination light in the exposure period during which the imager stores the electric charge.

4. The imaging system according to claim 3, wherein the illumination controller is configured to set a phase for the emission timing of the illumination light in the readout period to be a phase set in the exposure period of a frame chronologically previous to the readout period.

5. The imaging system according to claim 3, wherein the illumination controller is configured to set a phase for the emission timing of the illumination light in the readout period to be a phase set in the exposure period of a frame chronologically subsequent to the readout period.

6. The imaging system according to claim 3, wherein the illumination controller is configured to set a phase for the emission timing of the illumination light in the readout period to be an intermediate phase between phases set in the exposure periods of chronologically adjacent frames.

7. The imaging system according to claim 6, wherein the illumination controller is configured to set the phase for the emission timing of the illumination light in the readout period to be an average of phases set in the exposure periods of chronologically adjacent frames.

8. The imaging system according to claim 1, further comprising:
a vibration receiver configured to receive an input of a vibration of a vocal cord of the subject.

9. A processing device configured to be connected to an endoscope including an imager configured to read out an electric charge stored in a pixel by using a rolling shutter method, the processing device comprising:
a frequency detector configured to detect a frequency of a predetermined site of a subject; and
an illumination controller configured to control emission of an illumination light during a readout period of the signal value, wherein the illumination controller is configured to:
set a phase for an emission timing of the illumination light in an exposure period during which the imager stores the electric charge to be an identical phase at the frequency in each exposure period; and
refer to respective phases set in exposure periods of chronologically adjacent frames to set an emission timing of the illumination light in the readout period.

10. The processing device according to claim 9, wherein the illumination controller is configured to:
set a phase for the emission timing of the illumination light in the readout period to be an average of respective phases set in the exposure periods of chronologically adjacent frames; and
match an emission intensity of the illumination light in the readout period with an emission intensity of the illumination light in the exposure period during which the imager stores the electric charge.

11. The processing device according to claim 9, wherein the illumination controller is configured to:
set a phase for the emission timing of the illumination light in the exposure period during which the imager stores the electric charge to be an identical phase at the frequency in each frame; and
set an emission intensity of the illumination light in the readout period to be lower than an emission intensity of the illumination light in the exposure period during which the imager stores the electric charge.

12. The processing device according to claim 11, wherein the illumination controller is configured to set a phase for the emission timing of the illumination light in the readout period to be a phase set in the exposure period of a frame chronologically previous to the readout period.

13. The processing device according to claim 11, wherein the illumination controller is configured to set a phase for the emission timing of the illumination light in the readout period to be a phase set in the exposure period of a frame chronologically subsequent to the readout period.

14. The processing device according to claim 11, wherein the illumination controller is configured to set a phase for the emission timing of the illumination light in the readout period to be an intermediate phase between phases set in the exposure periods of chronologically adjacent frames.

15. The processing device according to claim 14, wherein the illumination controller is configured to set the phase for the emission timing of the illumination light in the readout period to be an average of phases set in the exposure periods of chronologically adjacent frames.

16. The processing device according to claim 9, wherein the frequency detector is configured to detect a frequency of a vocal cord of a subject.

17. An illumination control method implemented by an imaging system including: a light source configured to emit illumination light; and an imager configured to store an electric charge corresponding to an amount of received light and read out the stored electric charge as a signal value by using a rolling shutter method, the illumination control method comprising:
detecting a vibrational frequency of a predetermined site of a subject;
setting a phase for an emission timing of the illumination light in an exposure period during which the imager stores the electric charge to be an identical phase at the frequency in each frame; and
referring to respective phases set in exposure periods of chronologically adjacent frames to set an emission timing of the illumination light in a readout period of the signal value.

* * * * *